US012290424B2

(12) United States Patent
Kushnir et al.

(10) Patent No.: US 12,290,424 B2
(45) Date of Patent: May 6, 2025

(54) ASSEMBLY AND METHOD FOR THE PREPARATION OF A WOUND DRESSING

(71) Applicant: REDDRESS LTD., Pardes Hana (IL)

(72) Inventors: Alon Kushnir, Givat Ada (IL); Igal Kushnir, Pardes Hana (IL)

(73) Assignee: REDDRESS LTD., Pardes Hana (IL)

( * ) Notice: Subject to any disclaimer, the term of this patent is extended or adjusted under 35 U.S.C. 154(b) by 1323 days.

(21) Appl. No.: 16/649,821

(22) PCT Filed: Sep. 17, 2018

(86) PCT No.: PCT/IL2018/051051
§ 371 (c)(1),
(2) Date: Mar. 23, 2020

(87) PCT Pub. No.: WO2019/058375
PCT Pub. Date: Mar. 28, 2019

(65) Prior Publication Data
US 2020/0281775 A1    Sep. 10, 2020

(30) Foreign Application Priority Data
Sep. 24, 2017  (IL) ......................................... 254636

(51) Int. Cl.
*A61F 13/00* (2024.01)
*A61K 35/14* (2015.01)
*A61K 38/36* (2006.01)
*A61L 15/40* (2006.01)
(Continued)

(52) U.S. Cl.
CPC .. *A61F 13/00987* (2013.01); *A61F 13/00063* (2013.01); *A61K 35/14* (2013.01);
(Continued)

(58) Field of Classification Search
CPC ......... A61F 13/00987; A61F 13/00063; A61K 35/14; A61K 38/36; A61L 15/40;
(Continued)

(56) References Cited

U.S. PATENT DOCUMENTS 6,096,943 A * 8/2000 Maiwald ............... A61F 15/008
602/54
9,180,142 B2   11/2015 Kushnir et al.
(Continued)

FOREIGN PATENT DOCUMENTS

JP         5-508565 A       12/1993
KR   10-2011-0113754 A      10/2011
(Continued)

*Primary Examiner* — Jing Rui Ou
(74) *Attorney, Agent, or Firm* — Vorys, Sater, Seymour and Pease LLP; Anthony P. Venturino; Maryellen Feehery Hank

(57) ABSTRACT

Wound dressing assembly including (i) blood-clotting mold device having an enclosure defined between walls of a main body and a removable closure over an opening and configured for introduction of blood thereinto, and (ii) coagulation initiator in amount sufficient to coagulate blood introduced into the enclosure to form a blood clot. The formed blood clot is transferable onto a wound. Method for preparing a wound dressing by introducing a volume of blood into the enclosure of the blood-clotting mold device, maintaining the blood within the enclosure for time sufficient to permit clotting of the blood to obtain a blood clot; removing said the closure to open the enclosure; and extracting the blood clot from the enclosure. The formed blood clot may be used in a method for dressing a wound by fixation of the clot onto the wound.

7 Claims, 3 Drawing Sheets

(51) Int. Cl.
*A61M 1/36* (2006.01)
*A61M 35/00* (2006.01)

(52) U.S. Cl.
CPC .............. *A61K 38/36* (2013.01); *A61L 15/40* (2013.01); *A61M 1/36* (2013.01); *A61L 2300/418* (2013.01); *A61L 2400/04* (2013.01); *A61M 35/003* (2013.01)

(58) Field of Classification Search
CPC .......... A61L 2300/418; A61L 2400/04; A61M 1/36; A61M 35/003
See application file for complete search history.

(56) References Cited

U.S. PATENT DOCUMENTS

| | | | |
|---|---|---|---|
| 2005/0089551 A1* | 4/2005 | Recupero | A61L 15/44 424/443 |
| 2007/0055205 A1 | 3/2007 | Wright et al. | |
| 2010/0318052 A1* | 12/2010 | Ha | A61F 13/0226 604/385.01 |
| 2011/0318404 A1* | 12/2011 | Kushnir | A61K 9/7007 424/529 |
| 2017/0258877 A1* | 9/2017 | Bare | C12Y 304/21005 |

FOREIGN PATENT DOCUMENTS

| | | |
|---|---|---|
| KR | 20200074945 A | 6/2020 |
| WO | 2010/055622 A1 | 5/2010 |
| WO | 2010/086848 A2 | 8/2010 |

\* cited by examiner

ASSEMBLY AND METHOD FOR THE PREPARATION OF A WOUND DRESSING

TECHNOLOGICAL FIELD

This disclosure is in the field of wound treatment and concerns a wound dressing assembly for the preparation of a blood clot and use of this blood clot in wound treatment.

BACKGROUND

Chronic wounds and skin ulcers are a serious medical condition and effective wound treatment approaches is a recognized medical need.

U.S. Pat. No. 9,180,142 discloses a wound treatment procedure by which blood is coagulated and the so-formed blood clot is applied onto a wound with a dressing material.

GENERAL DESCRIPTION

The present disclosure concerns wound treatment through the use of a blood clot. Specifically provided by this disclosure is a wound dressing assembly (e.g. in the form of a kit-of-parts for use in the currently disclosed wound treatment) for preparing such a blood clot, a method for preparing a wound dressing comprising such a blood clot, and a method for dressing the wound therewith.

The blood clot that is formed and used according to this disclosure is typically, but not exclusively, formed from blood of the same subject whose wound is to be dressed by the teaching of this disclosure. The blood is typically whole blood withdrawn from the subject in any manner acceptable in medical practice for blood withdrawal. In some other embodiments, the blood is whole blood from a blood bank.

By a first of its aspects, the present disclosure provides a wound dressing assembly comprising a blood-clotting mold device having an enclosure, defined between walls of a main body and a removable closure (e.g. in the form of a film) that seals an opening of the enclosure (to maintain sterility of the enclosure), the enclosure being configured for introduction of blood thereinto, typically without removal of the closure or portion thereof. This device serves, as will be further understood from the description below, as a mold for forming a blood clot that is intended for placing onto a wound.

By one embodiment, at least one of the walls or closure of the device is pierceable by a needle and through the pierce formed therewith, blood is introduced into the sealed enclosure.

By another embodiment, the enclosure has a port for blood introduction; or at times two ports, one for introducing blood and the other for venting (e.g. to permit egress of gas from the enclosure during blood introduction). The venting port may be a priori sealed, intended for removal of excess pressure during injection of the blood into the enclosure. Typically, prior to injection of the blood and in order to permit such venting, the vent is opened.

By one other embodiment, the enclosure (prior to introducing the volume of blood) is under vacuum.

In some embodiments, the enclosure comprises a coagulation initiator in an amount sufficient to facilitate coagulation of blood introduced into the enclosure. The coagulation initiator may also be held in an independent container for either mixing with the blood before it is introduced into the enclosure or for independent injection into the enclosure before or after introducing the blood thereinto.

Blood coagulation initiators are known in the art. In one embodiment of the present disclosure, the blood coagulation initiator comprises at least kaolin. The blood coagulation initiator (kaolin or any other coagulation initiator) may be provided in any form, such as, liquid, powder, granulate, etc.

Once the blood clot is formed within the enclosure, it is transferable onto a wound or onto a dressing material.

The assembly preferably comprises a scaffold matrix (blood clot supporting matrix) within the enclosure that is intended for being integrated or embedded with the formed blood clot. The scaffold matrix may, thus, have the purpose of (i) providing an overall support to the blood clot; (ii) assisting in maintaining structural integrity of the clot once formed, and/or (iii) enabling the transfer of the clot to the wound or onto a dressing and supporting the clot throughout such transfer.

This supporting scaffold matrix is typically in a form of a net, such as a plastic net, a cloth etc. in some embodiments, the matrix is of a material similar to that of a dressing material, e.g. gauze.

The blood injection is, typically, performed such that said matrix will be embedded within the blood and hence within the subsequently formed blood clot The enclosure has a shape configured for extraction of the formed blood clot without compromising the integrity of the blood clot. For this, the opening of the enclosure that is initially sealed/closed by the closure, should be wide to permit such extraction, e.g. a shape of a relatively shallow cavity.

The mold device may have different shape and sizes to match different shapes and sizes of wounds.

In some embodiment, the enclosure has a shape and dimension that configures the eventual overall shape of the clotted blood mass formed within the enclosure and hence the shape and dimension of the blood clot subsequently applied onto the wound. The shape and dimension of the enclosure (and hence the shape and dimension of the eventual blood clot) may be designed according to the intended use and site of application. For a typical case of application onto a skin wound or ulcer, the enclosure is typically designed with an opening having a width sufficient to permit relatively easy extraction of the clot as whole without compromising its integrity. The clot is typically formed to have a horizontal dimension that is considerably larger than its height (thickness), e.g. in the form of a relatively shallow cavity as noted above. In some other embodiments, e.g. in the case of a tunneling wound, the relative dimension may be different and configured for such types of wounds.

In some embodiments, at least the walls of the main body are rounded (convex or U-shaped). Yet, in some other embodiments, the walls of the main body are polygonal, e.g. cubic shaped.

The enclosure may, by some embodiments, have the general form of a blister and the closure being a film that is removable from the rims of the main body. The enclosure may typically comprise a portion, e.g. all or parts of the main body, which is transparent.

Further, to facilitate transfer of the formed blood clot, without compromising the integrity of the clot, the enclosure is typically made of or is coated with a material of the kind to which a blood clot does not adhere or adheres to only weakly.

Also provided by this disclosure is a method for preparing a wound dressing making use of the blood-clotting mold device disclosed herein. Generally, the method comprises injecting a volume of blood into the enclosure of the of the currently disclosed blood-clotting mold device, permitting the volume of blood to clot to thereby obtain a blood clot within the device's enclosure, removing the closure and extracting the blood clot out of the enclosure.

By some embodiments, contemplated within the method of this disclosure, is a procedure by which a wall of the enclosure or the closure is first pierced to form a vent, e.g. by a sharp object or by a needle (e.g. the same needle subsequently used for injection of the blood) and only then blood is injected into the enclosure.

In some embodiments, after extraction, the blood clot may be combined with a dressing material. Such combination may involve transfer of the blood clot onto the dressing material for subsequent placing of the combined blood-clot and dressing material onto a wound; or placing the blood clot directly onto the wound and covering it with the dressing material. The dressing material may be gauze or any other material suitable or commonly used for dressing wounds.

Also provided by this disclosure is a method for dressing a wound. This method comprises the preparation of a blood clot and its extraction, in the manner described above and then applying the extracted blood clot onto a wound. Prior to or after application of the blood clot onto the wound, the blood clot may be combined with a wound dressing material as described above.

The assembly of this disclosure, which may be in the form of a kit-of-parts (collection of discrete elements), can comprise, in addition to the blood-clotting mold device, other elements for use in the methods disclosed herein.

Without being limited thereto, such other elements may include means for transferring the blood clot that has been formed in said enclosure onto the wound. Accordingly, in some embodiments, the assembly comprises a blood clot removing tool, e.g. a spoon-like or spatula-like instrument. This tool can be made of plastic, metal, wood, cardboard, silicon, or be made from any other suitable material, and is configured for the removal of the clot from the enclosure preferably in a manner that preserves the clot's structural integrity. In some embodiments, the removing tool is configured also for separating the blood clot from the wall of the enclosure.

In some embodiments, the assembly comprises means for securing the formed blood clot to the wound. Such means may be a dressing material, e.g. gauze or any other material that is or may be used in medical practice for dressing wounds.

In addition, or alternatively, the assembly may include elements such as those used for blood withdrawal, a blood collection vial, a blood coagulant to prevent premature coagulation of the blood (e.g. before introducing into the enclosure), blood removal and transfer tool, etc.

Reference is also made to U.S. Pat. No. 9,180,142, the relevant portions thereof being incorporated herein by reference.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

The embodiments illustrated in the annexed drawings include an enclosure in the form of a blister, which is an exemplary embodiment of the broader context of the present disclosure. Thus, this description of specific embodiments is intended for illustration of the more general principle of this disclosure and is not intended to be limiting.

Figure 1:
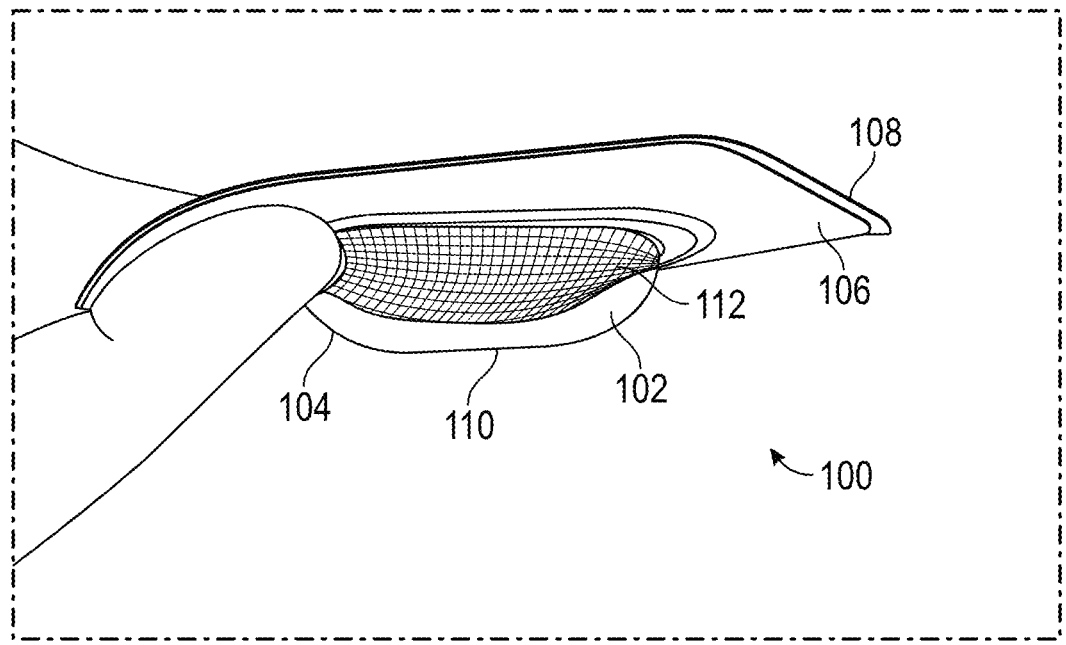
FIG. 1 is a picture providing a bottom perspective view of an enclosure, according to an embodiment of this disclosure, which is in the form of a blister.

Referring first to FIG. 1, shown is a picture of an enclosure generally designated 100 and in the shape of a blister, having a main body 102 with a blister depression 104 and a flat rim 106. Fitted onto the rim is a removable closure 108 in the form of a laminate/film.

Contained within the enclosure 100 is a coagulating initiator substance 110 which may be in the form of a liquid, powder, granulate, etc. The coagulation initiator may, for example, be kaolin. Also contained in the enclosure is a blood clot-supporting (scaffold) matrix 112 which may be made of gauze, of a polymeric mesh, etc., held at its peripheral portions between the rim and the closure and having a central portion within the enclosure.

Figure 2A:
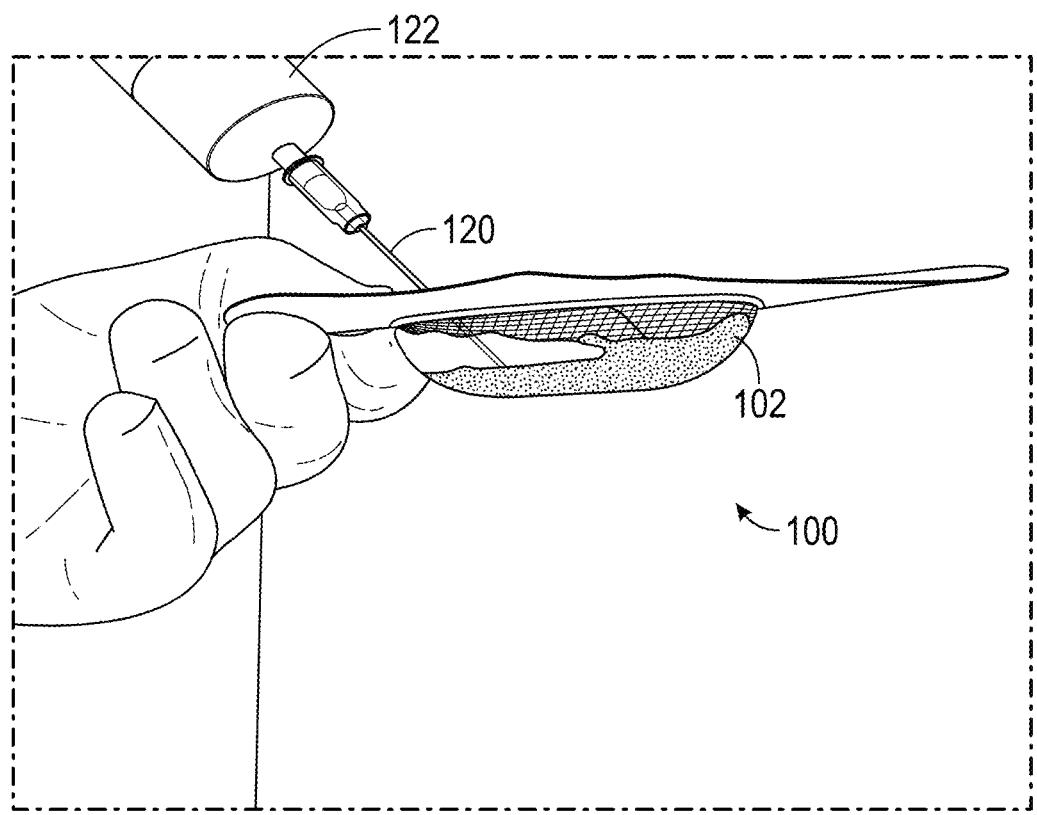
FIGS. 2A and 2B are side perspective views illustrating the injection of blood into the enclosure.
Figure 2B:
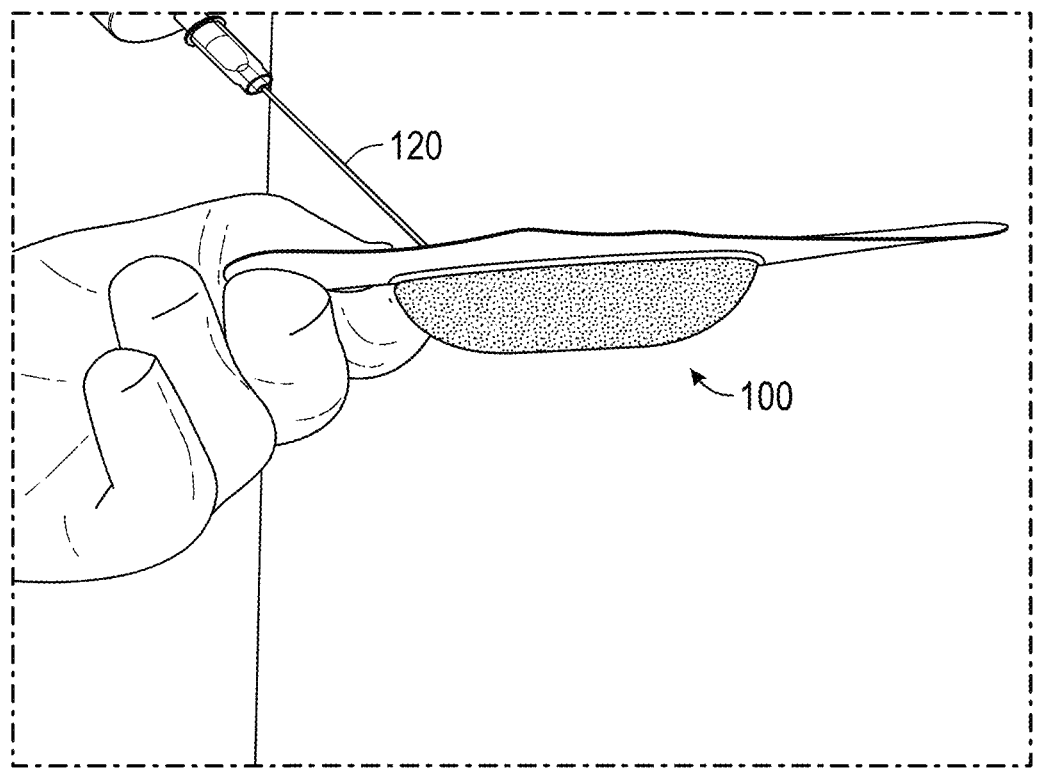

Blood, typically whole blood, is withdrawn and then injected into the enclosure, as shown in FIGS. 2A and 2B. Specifically, a needle 120 of a syringe 122 that contains the whole blood pierces the closure 108 and blood is injected until it fills a significant portion of the enclosure, sufficient to cover the blood clot-supporting scaffold matrix 112, as seen in FIG. 2B. It is possible, also, to initially pierce the closure so as to form a vent opening, e.g. by the blood injection needle, and inject the blood only subsequently.

Figure 3:
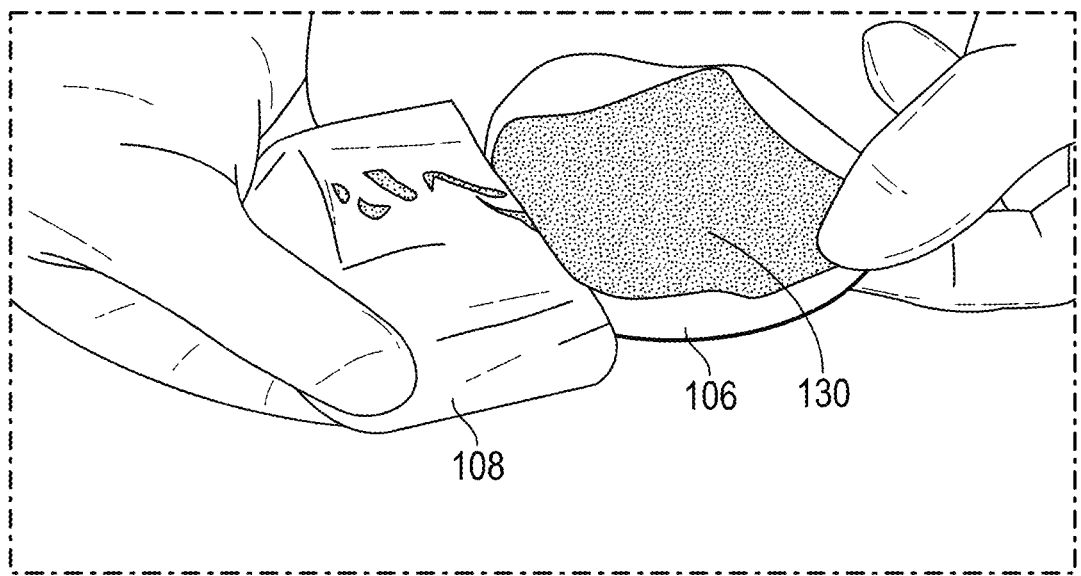
FIG. 3 shows the removal of the closure revealing the clot formed within the enclosure.

The blood is then maintained in the enclosure for a time sufficient for the blood to coagulate and after clotting the film 108 is removed to reveal a blood clot complex 130 that includes a blood clot 132 embedded with the blood clot-supporting scaffold matrix 112, as seen in FIG. 3.

Figure 4:
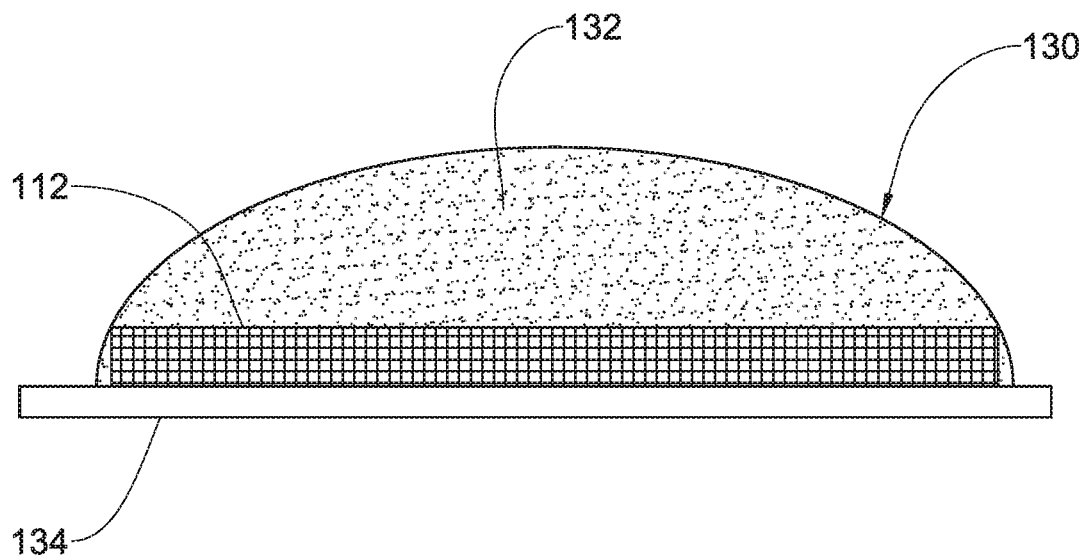
FIG. 4 is a schematic illustration of a wound dressing prepared according to an embodiment of this disclosure.

This blood clot complex 130 that includes the blood clot 132 and blood clot-supporting matrix 112 can then be combined with a dressing material 134, as seen in FIG. 4; the dressing material being, for example, gauze, to form a dressing-clot complex. This dressing-clot complex combination can be transferred onto the wound; alternatively, after opening of the cover of the blister and revealing the blood clot complex, as seen in FIG. 3, the blood clot complex can be transferred onto a wound and the dressing material applied thereon while the former is on the wound.

The invention claimed is:

1. A method for preparing a wound dressing, comprising:
introducing a volume of blood into an enclosure of a blood-clotting mold device, the enclosure
being in the shape of a blister having a main body with a blister depression having a blister wall and a flat rim, sealed by a removable closure, the enclosure
comprises a blood clot supporting matrix, and wherein the blood clot supporting matrix comprises gauze held at its peripheral portions between the rim and the closure and having a central portion within the enclosure, and
comprises a coagulation initiator,
wherein at least one of the blister wall and closure is pierceable by needle and said introducing comprises piercing one of the blister wall or closure with a needle and injecting the blood therethrough;

maintaining the blood within the enclosure for a time sufficient to permit clotting of the blood to thereby obtain a blood clot;

removing said closure to open the enclosure; and extracting the blood clot from the enclosure with said matrix.

2. The method of claim 1, wherein the enclosure is first pierced to form a vent and then the blood is injected.

3. The method of claim 1, wherein the blood is whole blood.

4. A method for dressing a wound, comprising:

introducing a volume of blood into an enclosure, the enclosure
- being in the shape of a blister having a main body with a blister depression with a blister wall and a flat rim, sealed by a removable closure,
- comprising gauze held at its peripheral portions between the rim and the closure and having a central portion within the enclosure, and
- comprising a coagulation initiator,
- wherein at least one of the blister wall and closure is pierceable by needle and said introducing comprises piercing one of the blister wall or closure with a needle and injecting the blood therethrough and allowing the blood clot to form on the gauze to be transferable thereby onto the wound;

maintaining the blood within the enclosure for a time sufficient to permit clotting of the blood to thereby obtain a blood clot;

removing said closure to open the enclosure;

extracting the blood clot from the enclosure, wherein said extracting comprises removal of the blood clot with the gauze; and fixing the blood clot onto the wound.

5. The method of claim 4, wherein the blood is whole blood.

6. The method of claim 1, wherein the blood injection is performed such that said matrix is embedded within the blood.

7. The method of claim 1, wherein the closure is a removable film.

* * * * *